United States Patent
McCurry et al.

(10) Patent No.: US 11,342,128 B2
(45) Date of Patent: May 24, 2022

(54) ELECTROLYTIC CAPACITOR

(71) Applicant: Pacesetter, Inc., Sylmar, CA (US)

(72) Inventors: Troy McCurry, West Union, SC (US);
Peter J. Fernstrom, Pickens, SC (US);
Ralph Jason Hemphill, Sunset, SC (US)

(73) Assignee: Pacesetter, Inc., Sylmar, CA (US)

( * ) Notice: Subject to any disclaimer, the term of this patent is extended or adjusted under 35 U.S.C. 154(b) by 185 days.

(21) Appl. No.: 16/694,655

(22) Filed: Nov. 25, 2019

(65) Prior Publication Data

US 2020/0176193 A1    Jun. 4, 2020

Related U.S. Application Data

(60) Provisional application No. 62/773,549, filed on Nov. 30, 2018.

(51) Int. Cl.
| | | |
|---|---|---|
| *H01G 9/055* | (2006.01) | |
| *A61N 1/39* | (2006.01) | |
| *H01G 9/008* | (2006.01) | |
| *H01G 11/26* | (2013.01) | |
| *H01G 9/02* | (2006.01) | |
| *H01G 9/14* | (2006.01) | |

(52) U.S. Cl.
CPC ........... *H01G 9/055* (2013.01); *A61N 1/3956* (2013.01); *H01G 9/008* (2013.01); *H01G 9/02* (2013.01); *H01G 9/14* (2013.01); *H01G 11/26* (2013.01)

(58) Field of Classification Search
CPC .......... H01G 9/042; H01G 9/04; H01G 9/055; H01G 9/14; H01G 11/26; A61N 1/3956
See application file for complete search history.

(56) References Cited

U.S. PATENT DOCUMENTS

| | | | | |
|---|---|---|---|---|
| 3,611,051 | A * | 10/1971 | Puppolo | H01G 9/00 361/531 |
| 5,814,082 | A | 9/1998 | Fayram et al. | |
| 5,930,109 | A * | 7/1999 | Fishler | H01G 9/04 361/508 |
| 6,032,075 | A | 2/2000 | Pignato et al. | |
| 6,141,205 | A | 10/2000 | Nutzman et al. | |
| 7,206,191 | B2 * | 4/2007 | Sherwood | H01G 9/008 361/503 |
| 7,531,010 | B1 | 5/2009 | Feger et al. | |
| 7,564,677 | B2 * | 7/2009 | Poplett | H01G 9/004 361/508 |
| 8,761,875 | B2 * | 6/2014 | Sherwood | A61N 1/3906 607/5 |
| 8,873,220 | B2 * | 10/2014 | Sherwood | H01G 9/02 361/503 |

* cited by examiner

*Primary Examiner* — Eric W Thomas

(57) ABSTRACT

The electrolytic capacitor has a conductive sheet with a central portion defined by a peripheral edge, a first tail extending out from the peripheral edge in a first direction, and a second tail extending out from the peripheral edge in a second direction. The second direction is opposite the first direction. The first tail and the second tail each have a free end with a first recess at the free.

18 Claims, 13 Drawing Sheets

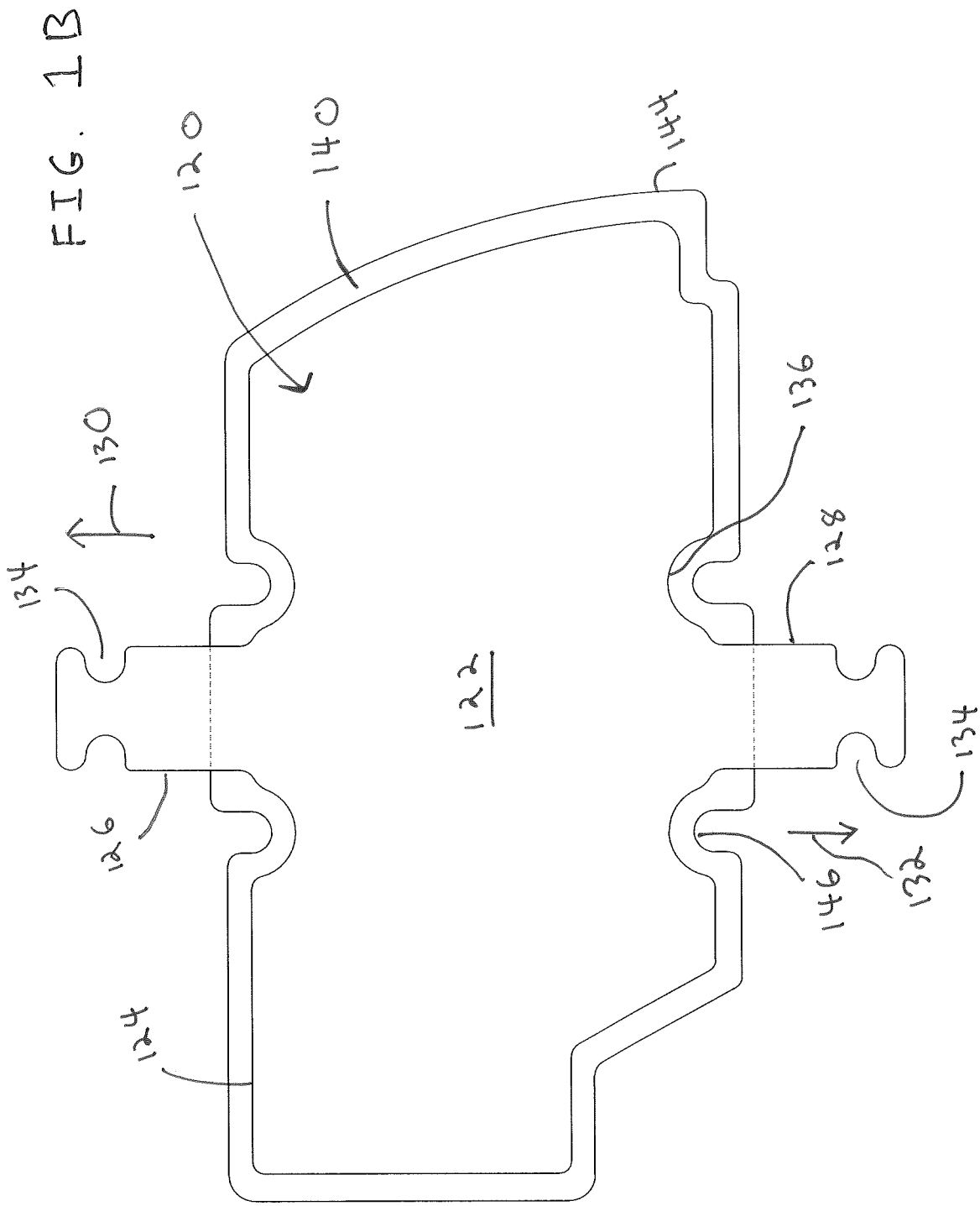

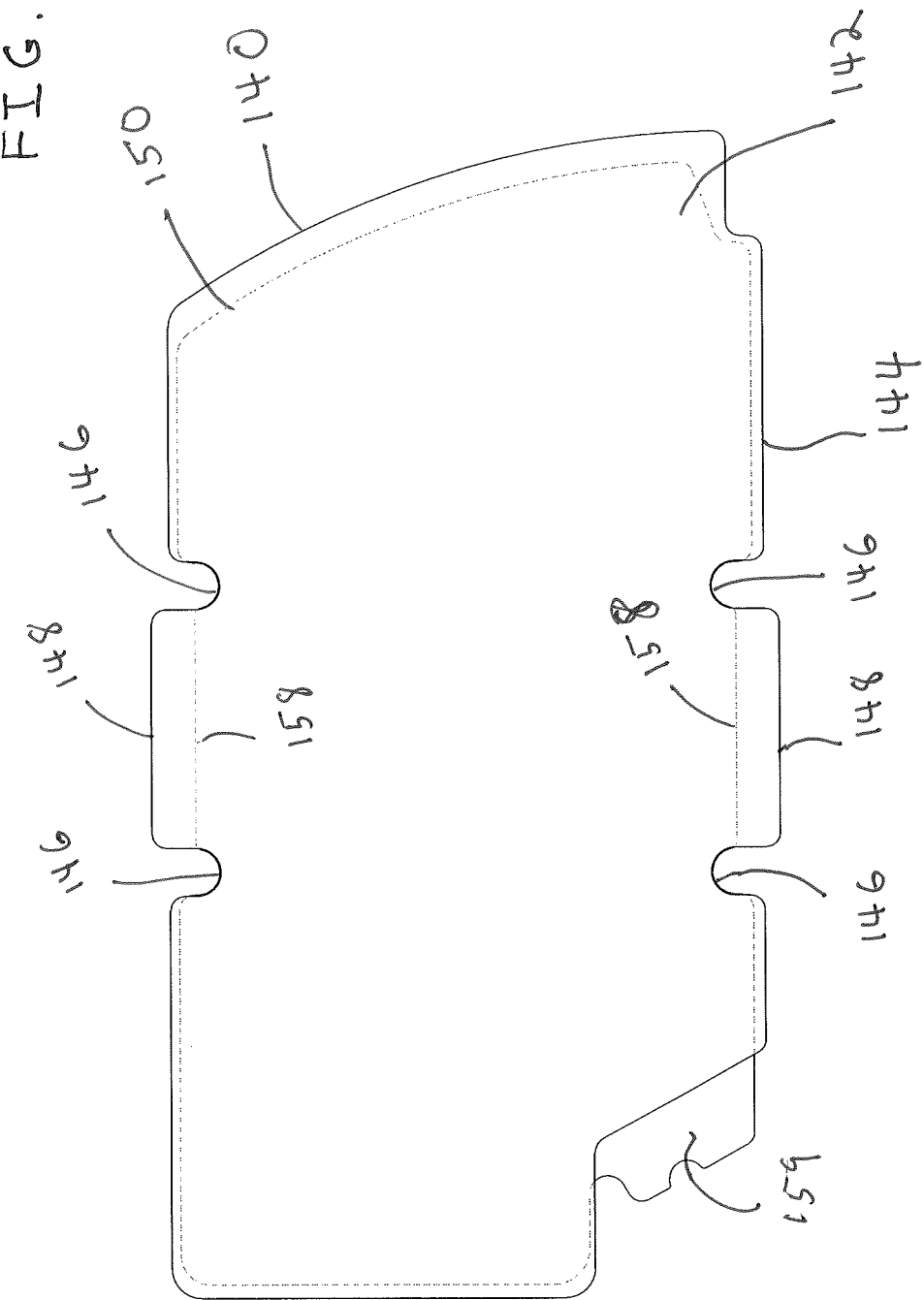

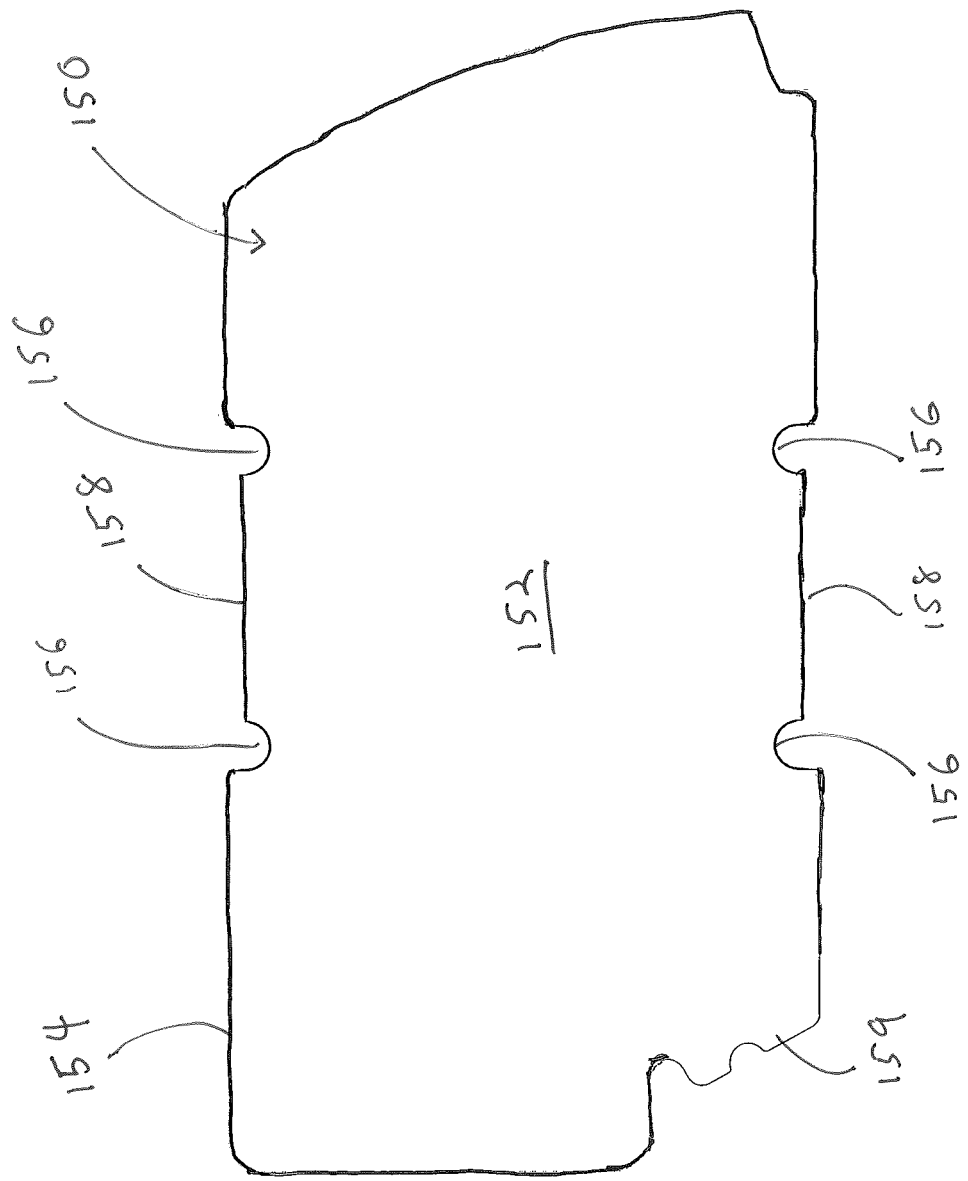

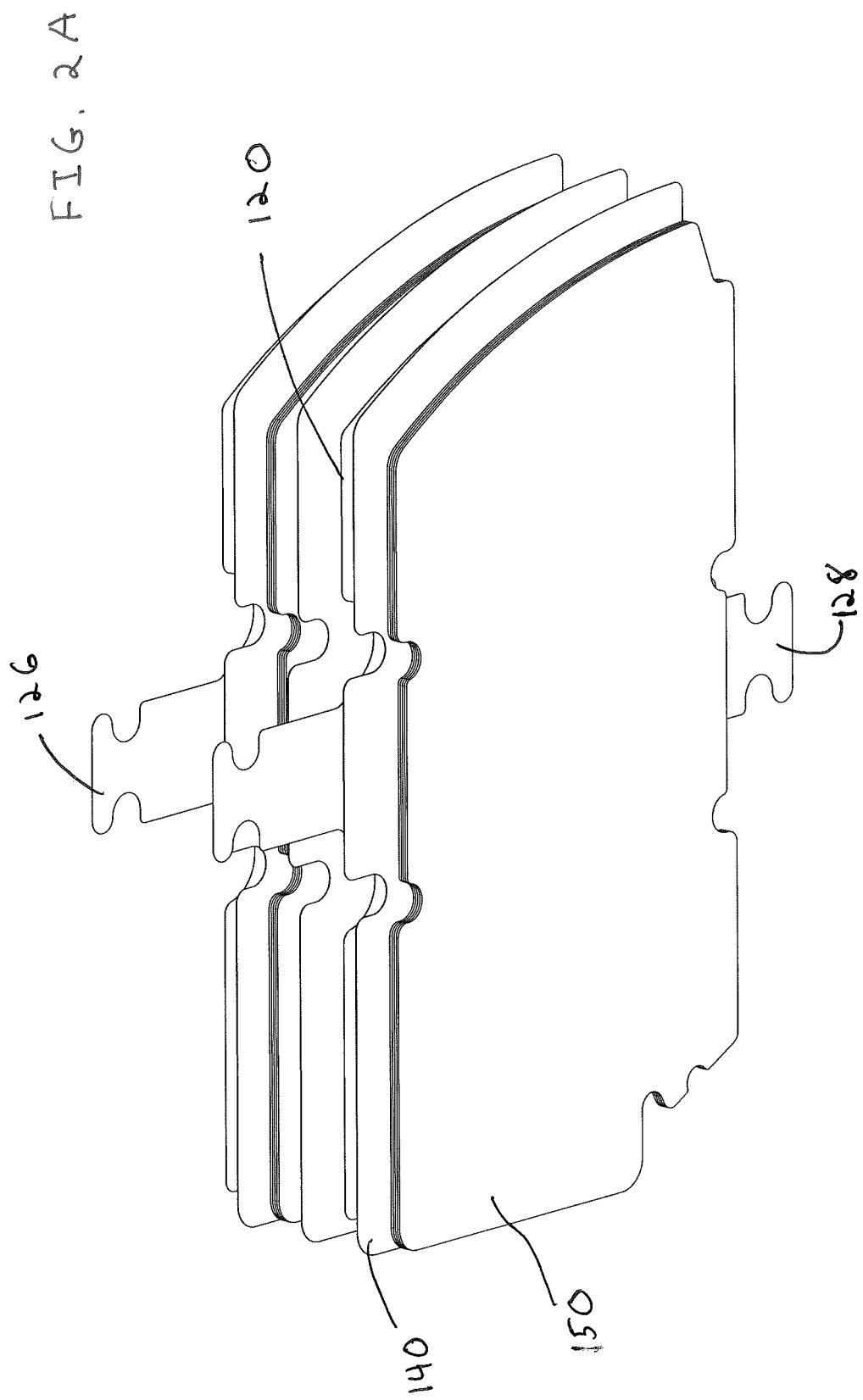

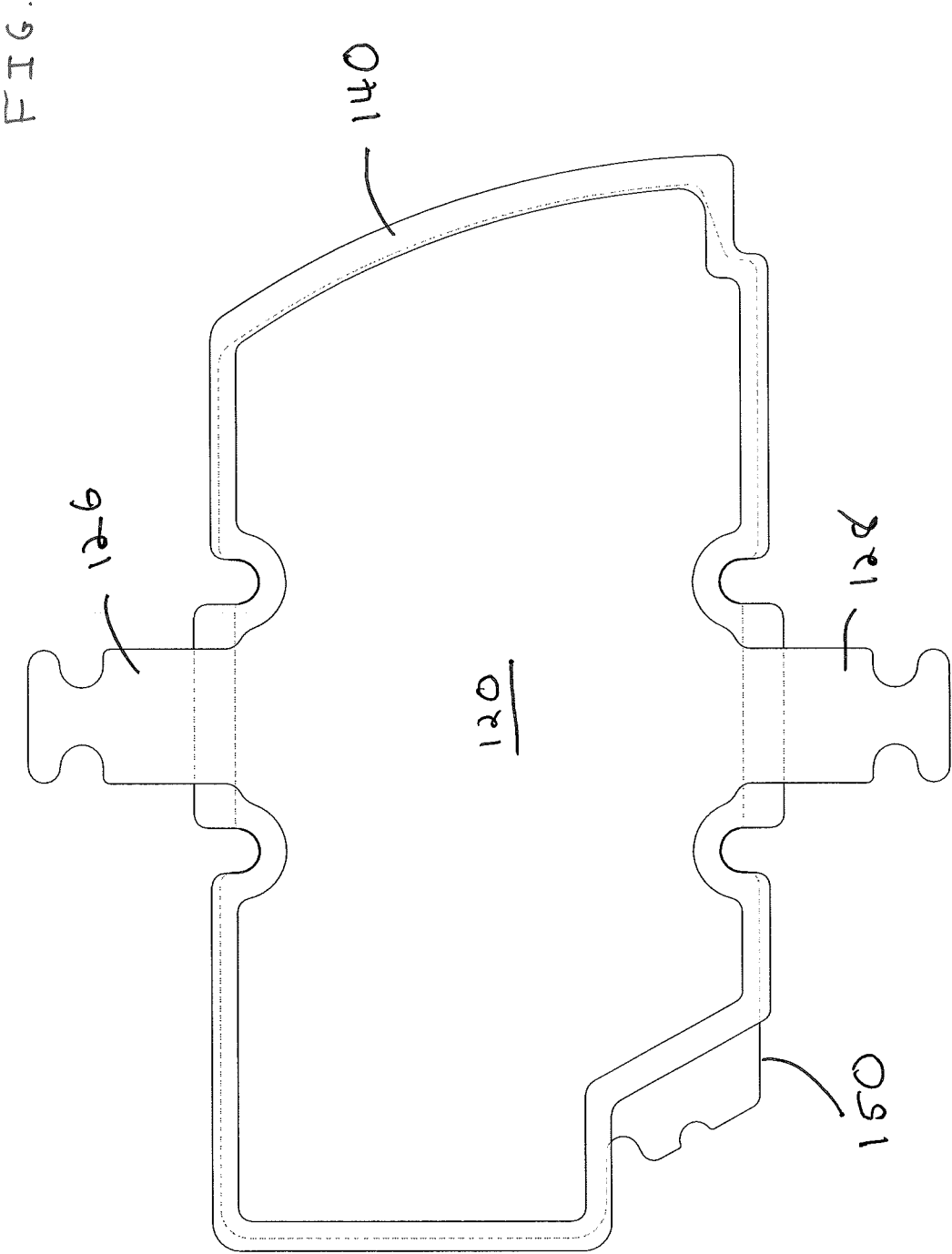

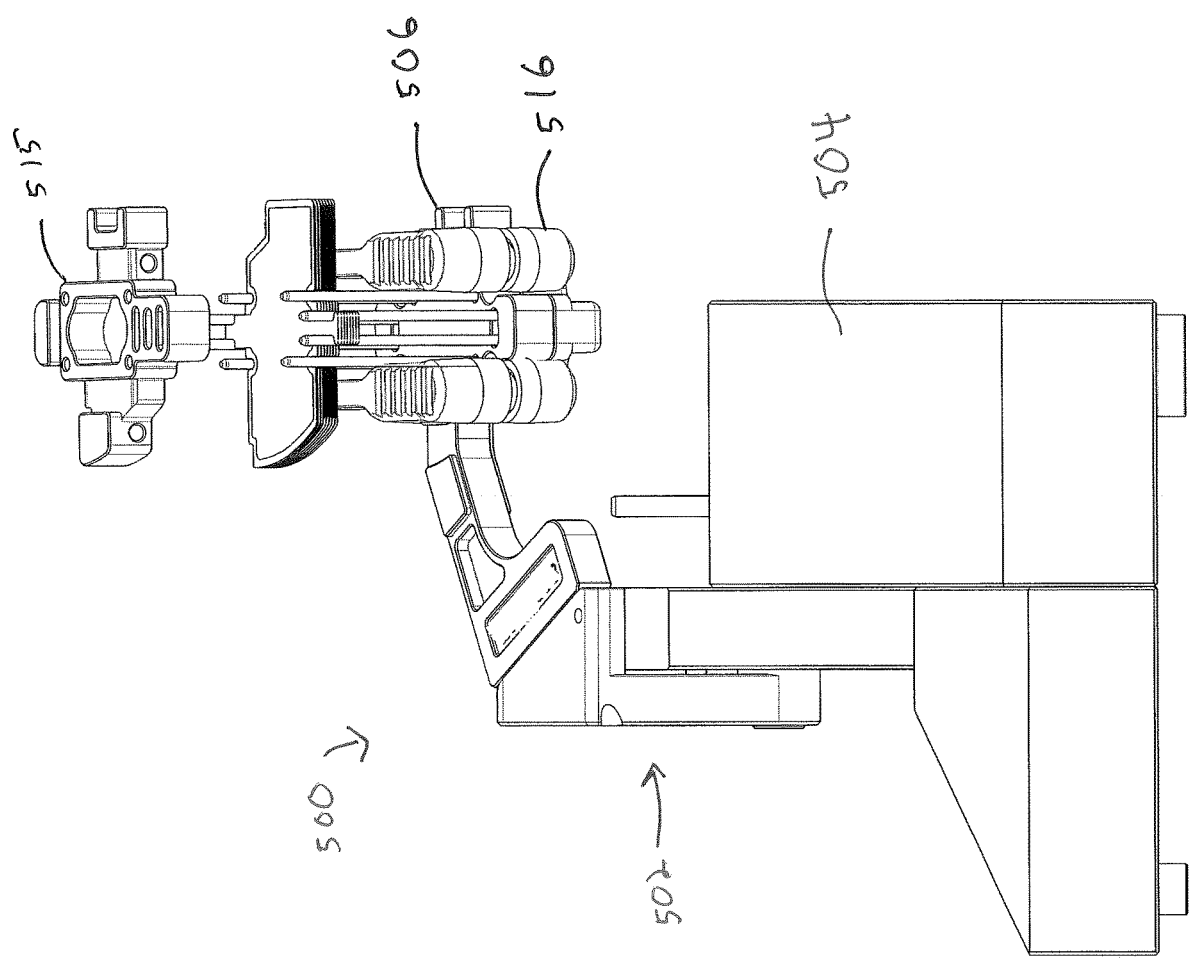

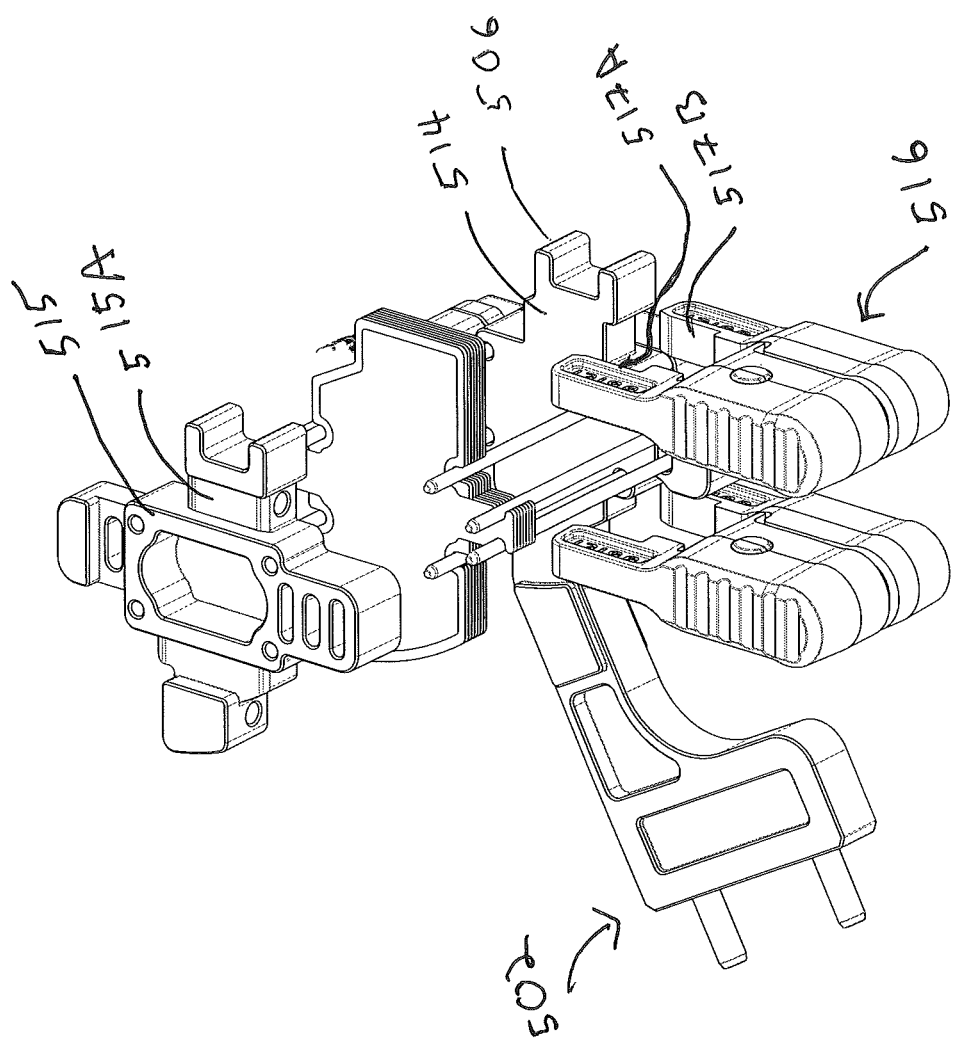

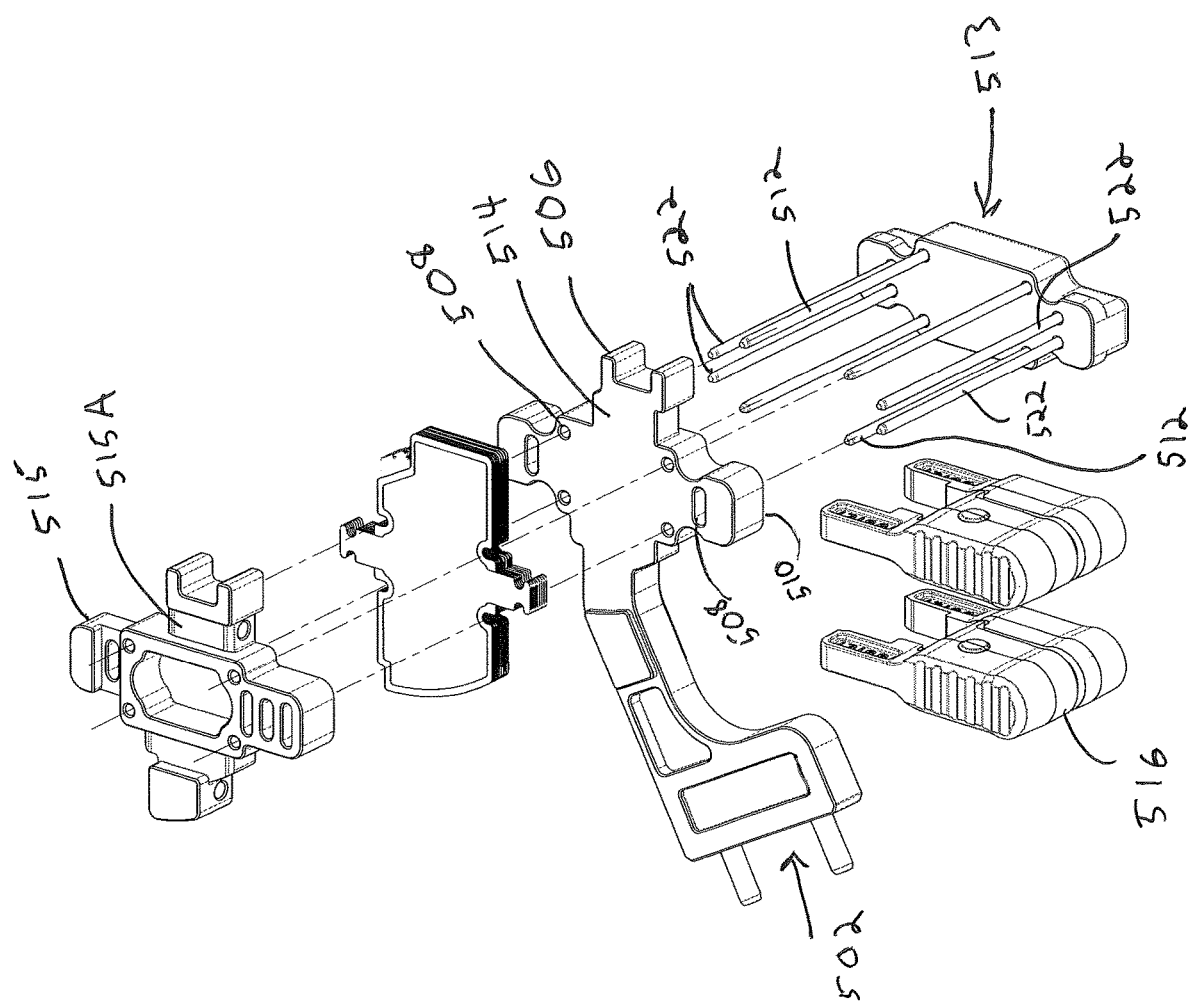

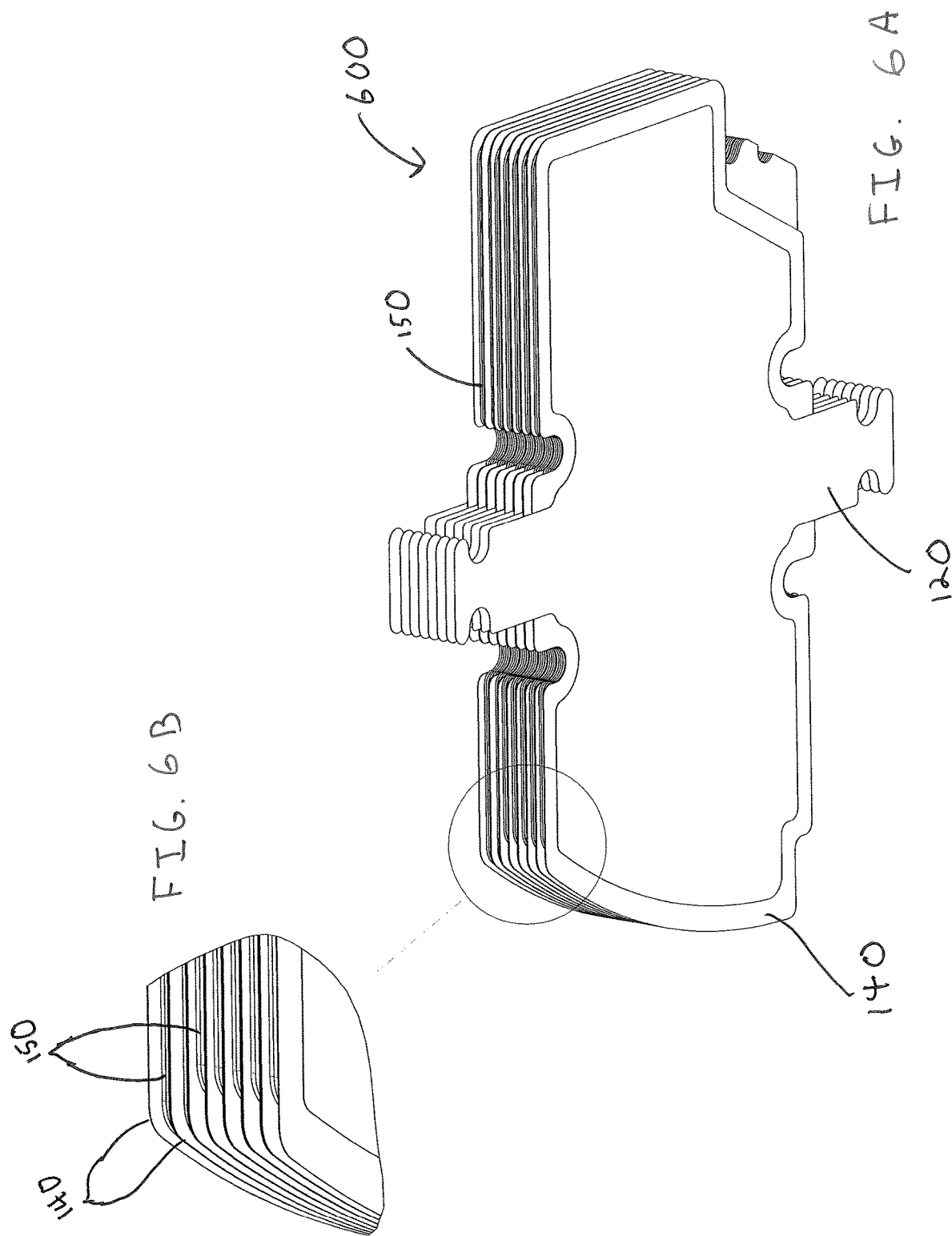

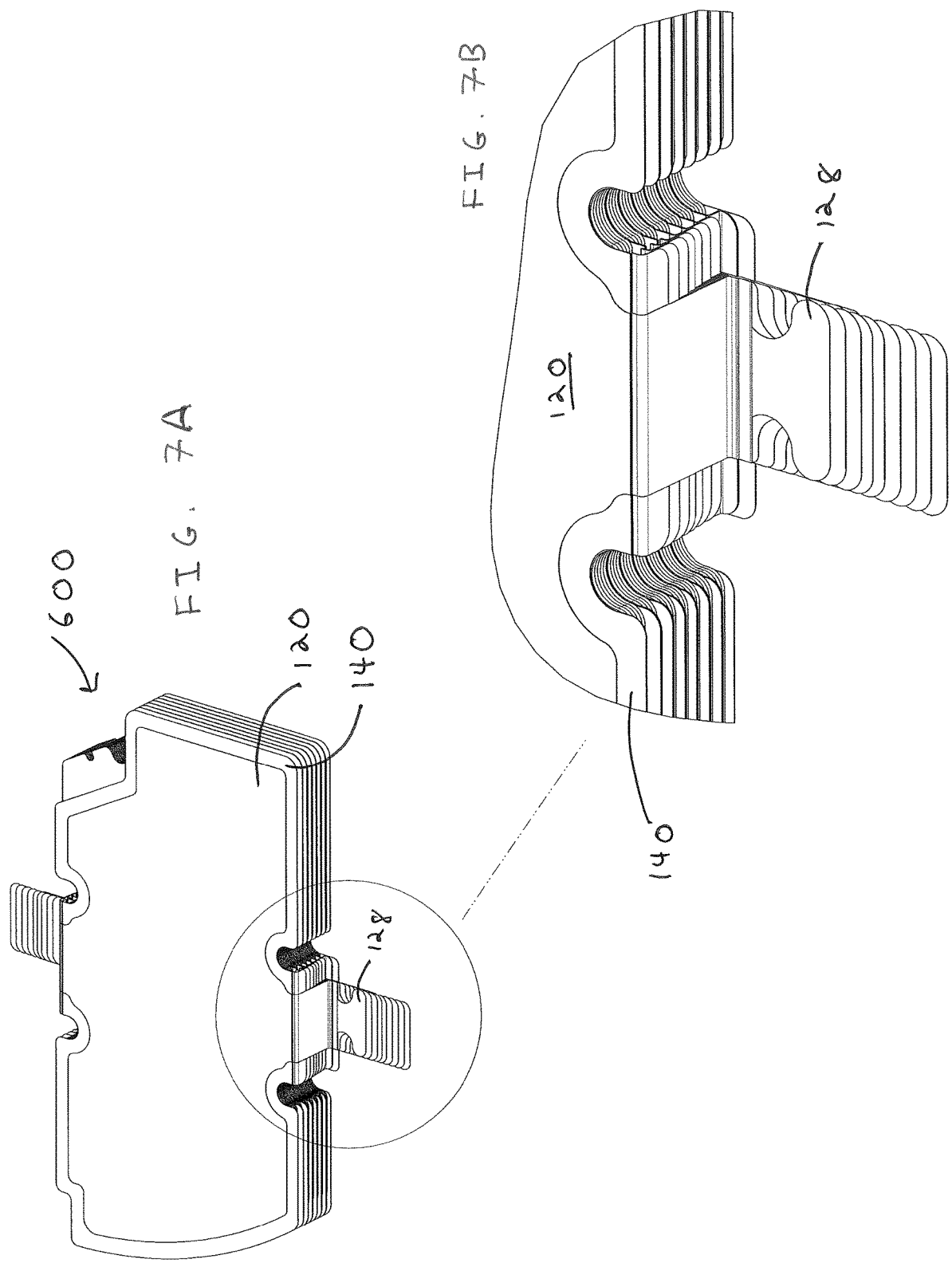

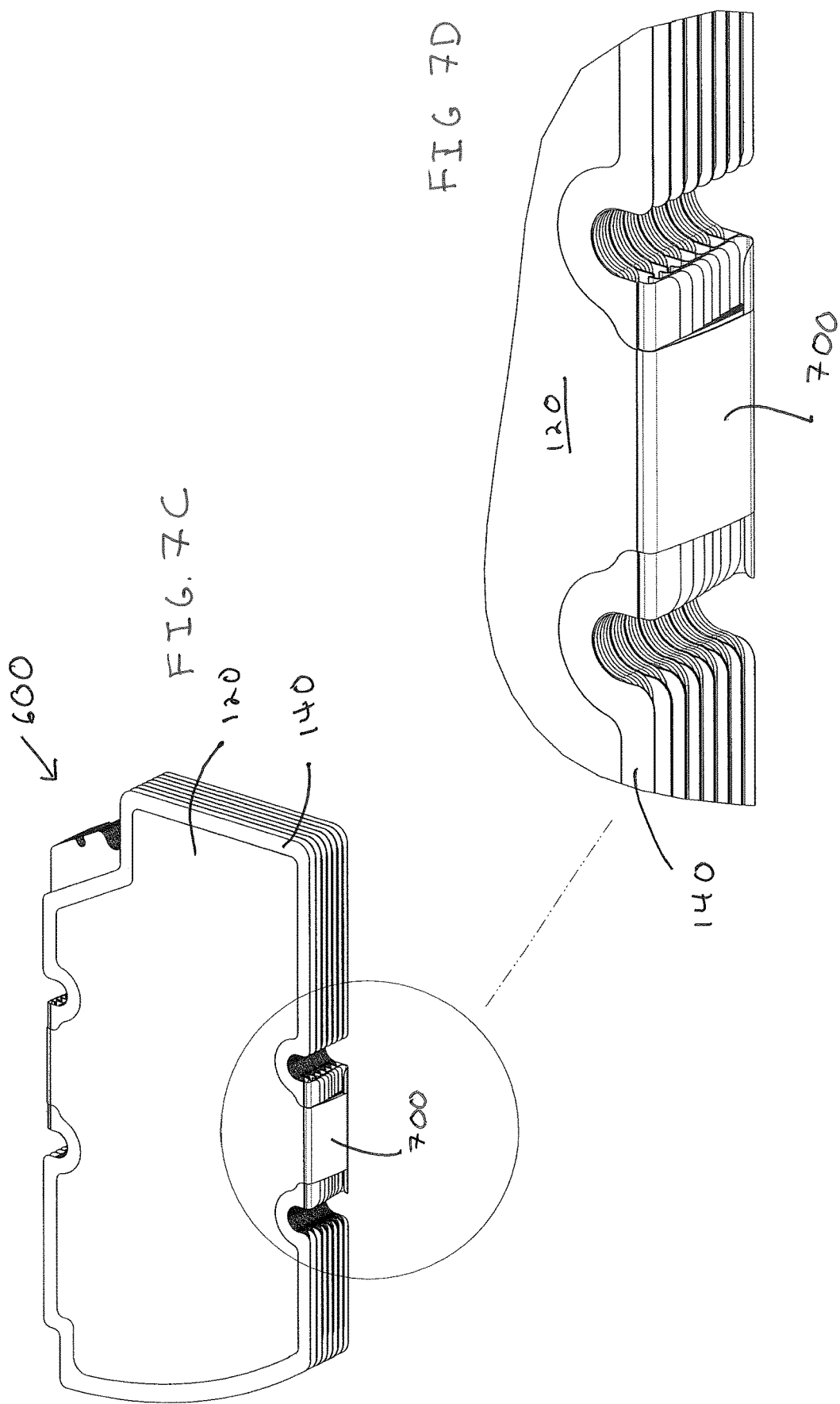

ELECTROLYTIC CAPACITOR

FIELD OF THE INVENTION

This application claims the benefit of U.S. Provisional Patent Application No. 62/773,546, filed on Nov. 30, 2018. The patent application identified above is incorporated here by reference in its entirety to provide continuity of disclosure.

FIELD

The present disclosure relates generally to the field of electrolytic capacitors and batteries.

BACKGROUND

Compact, high voltage capacitors are utilized as energy storage reservoirs in many applications, including implantable medical devices. These capacitors are required to have a high energy density, since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Stacked electrolytic capacitors are typically constructed with a plurality of anodes and cathodes, which must be separated by a liquid-absorbent insulating material, i.e., a separator, which is impregnated by an electrically conductive electrolyte. If the separator is not present as a line of sight barrier between any anode and adjacent cathode, there exists a danger of physical contact, as well as electrical breakdown of any incidental gasses present in the completed capacitor. Either of these scenarios would result in an undesirable partial or complete discharge event with a high probability of device failure.

Stacked electrolytic capacitors have utilized physical features in the constituent components of assembly with the aim of assuring precision of physical alignment such that the dimensions of those components leave physical margins that assure adequate separator coverage between all anodes and cathodes. Historically, those features have included holes in the separators, anodes, and cathodes in order to align with features on stacking fixtures when being assembled. These holes undesirably lessen the surface area in each anode and cathode, which in turn requires compensation either in the number of anodes and cathodes, or in the overall physical outline of those components in order to achieve a given design capacitance in the finished part.

The stacked alignment holes result in an undesirably larger overall finished part than would otherwise be required. The stacked alignment holes also create isolated cavities in the finished part that can lead to gas rich, electrolyte starved regions ripe for latent failure. The edges of the holes or other alignment features necessarily create more edge length and complexity of shape for each anode, which increases the challenge of removing them flaw free from the source anode sheet material. Additionally, alignment holes result in deformation and leakage current due to an inferior oxide layer formed on edge surfaces of the holes during aging.

The manufacture of a stacked capacitor therefore presents a challenge which must be addressed.

BRIEF SUMMARY

Electrolytic capacitors, and methods and apparatus for making the same are disclosed in herein.

One aspect of the present disclosure relates to a cathode. The cathode includes a conductive sheet having a central portion defined by a peripheral edge, a first tail extending out from the peripheral edge in a first direction, and a second tail extending out from the peripheral edge in a second direction opposite the first direction, wherein each of the first tail and the second tail has a first recess at a free end thereof.

Another aspect of the present disclosure relates to a device. The device includes a conductive anode, a dielectric material disposed on a surface of the conductive anode, a conductive cathode, a separator disposed between the anode and the cathode, and an electrolyte disposed between the anode and the cathode, wherein the conductive cathode includes: a first conductive sheet having a central portion defined by a peripheral edge, a first tail extending out from the peripheral edge in a first direction, and a second tail extending out from the peripheral edge in a second direction opposite the first direction, wherein each of the first tail and the second tail has a first recess at a free end thereof.

BRIEF DESCRIPTION OF THE DRAWINGS

FIG. 1B illustrates a cathode according to an embodiment of the present disclosure.

FIG. 1C illustrates a separator according to an embodiment of the present disclosure.

FIG. 1D illustrates an anode according to an embodiment of the present disclosure.

FIG. 2A is an exploded, perspective view of a capacitor stack according to an embodiment of the present disclosure.

FIG. 2B is a plan view of the capacitor stack of FIG. 2A.

FIG. 4 is a perspective view of an apparatus for manufacturing a stacked electrolytic capacitor configuration, according to an embodiment of the present disclosure.

FIG. 5A is a perspective view of a portion of the apparatus of FIG. 4.

FIG. 5B is an exploded, perspective view of a portion of the apparatus of FIG. 4.

FIG. 6A is a perspective view of a stacked electrolytic capacitor configuration including anodes, cathodes and separator sheets according to an embodiment of the present disclosure.

FIG. 6B is an enlarged view of a portion of the stacked electrolytic capacitor configuration of FIG. 6A.

FIG. 7A is a perspective view of a stacked electrolytic capacitor configuration including anodes, cathodes and separator sheets at a step of manufacture, according to an embodiment of the present disclosure.

FIG. 7B is an enlarged view of a portion of the stacked electrolytic capacitor configuration of FIG. 7A.

FIG. 7C is a perspective view of the stacked electrolytic capacitor configuration of 7A at another step of manufacture, according to an embodiment of the present disclosure.

FIG. 7D is an enlarged view of a portion of the stacked electrolytic capacitor configuration of FIG. 7C.

DETAILED DESCRIPTION

The following detailed description of capacitor and battery designs refers to the accompanying drawings that illustrate exemplary embodiments consistent with these devices. Other embodiments are possible, and modifications may be made to the embodiments within the spirit and scope of the methods and systems presented herein. Therefore, the following detailed description is not meant to limit the devices described herein. Rather, the scope of these devices is defined by the appended claims.

Figure 1A:
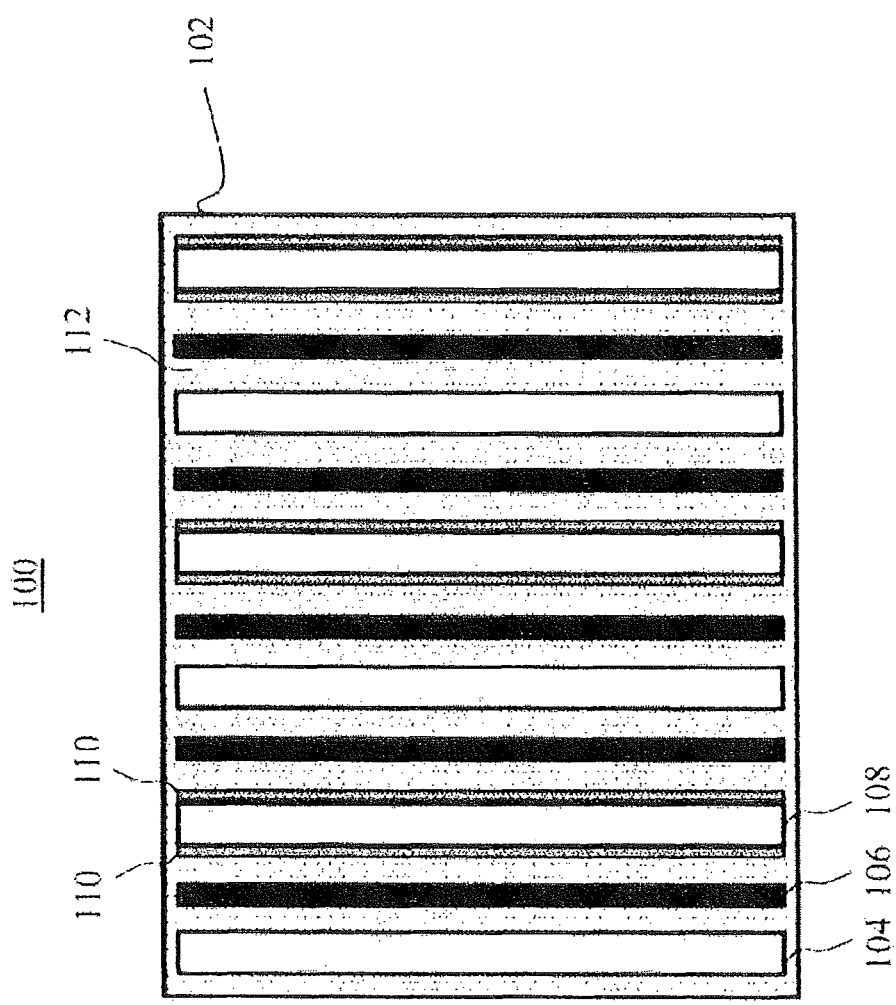
FIG. 1A illustrates a cross-section of an electrolytic capacitor or battery.

FIG. 1A illustrates a cross-sectional view of an electronic component 100 according to one embodiment of the disclosure. Electronic component 100 includes a housing 102 that contains a plurality of cathodes 104 alternating with a plurality of anodes 108, and separated by a plurality of separators (or spacers) 106. Each anode 108 includes a dielectric material 110 on or around an outer surface of anode 108. Dielectric material 110 may be an oxide that is thermally grown on, or deposited onto, the surface of anode 108. A high-k dielectric material may be used for dielectric material 110. A conductive electrolyte 112 fills the spaces between each of the elements within housing 102. Electrolyte 112 may be a polymer or liquid electrolyte as would be understood by one skilled in the art. Example electrolytes include ethylene glycol/boric acid-based electrolytes and anhydrous electrolytes based on organic solvents such as dimethylformamide (DMF), dimethylacetamide (DMA), or gamma-butyrolactone (GBL). The plurality of cathodes 104 may be electrically connected to a single, common cathode terminal, while the plurality of anodes 108 may be similarly connected to a single, common anode terminal.

Electronic component 100 may be, for example, an electrolytic capacitor or a battery. When electronic component 100 is used as a capacitor, example materials for the plurality of cathodes 104 include aluminum, titanium, and stainless steel, while example materials for the plurality of anodes 108 include aluminum and tantalum. When electronic component 100 is used as a battery, example materials for the plurality of cathodes 104 include silver vanadium oxide, carbon fluoride, magnesium oxide, or any combination thereof, while example materials for the plurality of anodes 108 include lithium metal.

Spacer 106 may be provided to maintain a given separation between each cathode 104 and an adjacent anode 108 within housing 102. Additionally, spacer 106 may be provided to prevent arcing between cathode 104 and anode 108 in spaces where dielectric 110 may be very thin or nonexistent, and/or where a void within electrolyte 112 exists between cathode 104 and anode 108.

Aligning each cathode 104, spacer 106, and anode 108 together in a stack is typically performed using physical features on each element that fit together (such as a peg-in-hole arrangement). As discussed above, this reduces the total usable surface area of the stack elements, which in turn reduces the overall energy density of electronic component 100.

It should be understood that the various elements and dimensions of electronic component 100 are not drawn to scale. Although each of cathode 104, separator 106, and anode 108 are illustrated as being apart from one another for the convenience of illustration and labeling, it would be understood by one skilled in the art that such elements may also be stacked together in close physical contact with one another.

FIGS. 1B-1D respectively illustrate embodiments of a cathode, anode and separator according to an embodiment of the present disclosure.

FIG. 1B illustrates a cathode 120 according to an embodiment of the present disclosure. The cathode 120 includes a central portion 122 defined by a peripheral edge 124, a first tail 126 and a second tail 128. The first tail 126 extends outward from the peripheral edge 124 in a first direction 130. The second tail 130 extends outward from the peripheral edge 124 in a second direction 132, the second direction 132 being opposite from the first direction 130.

The peripheral edge 124 of the cathode 120 includes several recesses, some of which are utilized as alignment guides when the cathode 120 is stacked with other components, e.g., a plurality of cathodes, anodes, and separators, into a capacitor stack. Each of the first and second tails 126, 128 includes at least one first recess at a distal end thereof. In FIG. 1B, each of the first and second tails 126, 128 includes two first recesses 134 at the distal end thereof. The first recesses 134 are utilized to align the cathode 120 with other components of a capacitor stack, such as a separator 140 and/or anode 150 described below.

The central portion 122 includes at least two second recesses extending inward from the peripheral edge 124. The second recesses are located adjacent to a proximal end of the first and second tails 126, 128. In FIG. 1B, the central portion 122 includes a pair of second recesses 136 located adjacent to, and on opposing sides of, the proximal end of the first tail 126, and another pair of second recesses 136 adjacent to, and on opposing sides of, the proximal end of the second tails 128. The second recesses 136 are present so that cathode 120 does not interfere with corresponding alignment features of the other components, such as the separator 140 and the anode 150, and do not participate in the alignment of the cathode 120 in the capacitor stack. Alignment of the cathode 120 in the capacitor stack is achieved by the first recesses 134 present in the tails 126, 128.

Cathode 120 may be commonly formed from a foil or plate made of a metal, such as aluminum, titanium or stainless steel, or of any electrically conductive material that can be formed into a uniform, thin sheet. The cathode tails 126, 128 may be extensions of the material forming the cathode 120, or may be a different material that is bonded to cathode 120. The terms "foil," "sheet," and "plate" are used interchangeably hereinto refer to a thin, planar material.

FIG. 1C illustrates a separator in accordance with an embodiment of the present disclosure. The separator 140 includes a non-conductive sheet 142 defined by a peripheral edge 144. The separator includes recesses extending inward from the peripheral edge 144 that are utilized as alignment guides when the separator is stacked with other components to form a capacitor stack. The separator 140 may include at least two third recesses 146. In FIG. 1C, the separator 140 includes four third recesses 146. The third recesses 146 may be positioned along the peripheral edge 144 of the sheet 142 such that the separator is immobilized during alignment. In FIG. 1C, one pair of third recesses 146 is located on one side of the sheet 142 and another pair of third recesses 146 is located on an opposite side of the sheet 142. Edge portions 148, which are formed between each pair of third recesses, align with the tails 126, 128 of the cathode 120 as illustrated in FIG. 1B. In some embodiments, the edge portions 148 align with the portions of the peripheral edge 144 on opposite sides of the third recesses 146. Alternatively, as illustrated in FIGS. 1B and 1C, the edge portions 148 project further outward and beyond the portions of the peripheral edge 144 on opposite sides of the third recesses 146.

In one embodiment, the separator 140 may include a high density Kraft paper. Other example materials include woven textiles made of one or a composite of several nonconductive fibers, such as aramid, polyolefin, polyamide, polytetrafluoroethylene, polypropylene, and glass. Separator 140 should be porous enough for an electrolyte to penetrate therethrough. Any insulating material that can be formed into a uniform, thin sheet with a porous structure may be used for the separator 140. The insulating material preferably shows no dissolution or shrinkage when introduced to the electrolyte. Similarly, when introduced to the electrolyte, the insulating material preferably does not elute any chemicals (e.g., corrosives or, in the case of aluminum electrolytic capacitors, halides) that would damage any part of a battery device over time.

Referring again to FIG. 1B, the separator 140 (shown underlying the cathode 120) has a larger surface area than the central portion 122 of the cathode 120, and the peripheral edge 144 of the separator 140 extends outward from the peripheral edge 124 of the central portion 122. The larger area of the separator 140 compared to that of the central portion 122 of the cathode 120 is to prevent a line of sight between the cathode 120 and an anode. The pairs of third recesses 146 of the separator 140 align with the pairs of second recesses 136 of the central portion 122 of the cathode 120. As shown in FIG. 1B, each pair of third recesses 146 of the separator align with the cathode 120 such that the third recesses in a pair are disposed on opposite sides of the proximal end of a tail 126, 128. Due to the larger area of the separator 140, the peripheral edge of each third recess 140 extends outward beyond the peripheral edge of the corresponding second recess 136 of the cathode 120. Accordingly, when stacked, the third recesses of the separator 140 participate in the alignment of the separator in the capacitor stack. The second recesses 136 of the cathode 120 may function as a coarse alignment guide for the cathode 120. Fine alignment of the cathode 120 is achieved by the first recesses 134.

FIG. 1D illustrates an anode in accordance with an embodiment of the present disclosure. The anode 150 includes a conductive sheet 152 defined by a peripheral edge 154. The anode includes recesses extending inward from the peripheral edge 154 that are utilized as alignment guides when the anode is stacked with other components to form a capacitor stack. The anode 150 may include at least two fourth recesses 156. In FIG. 1D, the anode 150 includes four fourth recesses 156. The fourth recesses 156 may be positioned along the peripheral edge 154 of the sheet 152 such that the anode is immobilized during alignment. In FIG. 1D, one pair of fourth recesses 156 is located on one side of the sheet 152 and another pair of fourth recesses 156 is located on an opposite side of the sheet 152. Edge portions 158, which are formed between each pair of fourth recesses, align with the tail portions 126, 128 of the cathode 120. In some embodiments, the edge portions 158 align with the portions of the peripheral edge 154 on opposite sides of the fourth recesses 156. Alternatively, as illustrated in FIG. 1D, the edge portions 158 are disposed inward of the portions of the peripheral edge 154 on opposite sides of the fourth recesses 156. The inward position of the edge portions 158 may further avoid a line of sight with a tail portion of the cathode 120.

Returning to FIG. 1C, an outline of the anode 150 (in dashed lines underlying the separator 140) illustrates that the anode 150 has a surface area that is equal to or less than that of the separator 140. The edge portion 148 of the separator 140 extends outward and beyond the edge portion 158 of the anode 150. A portion 159 of the anode 150 at which a terminal connection is made extends outward and beyond the peripheral edge 144 of the separator 140. FIGS. 2A and 2B illustrate a capacitor stack which includes cathodes 120, separators 140 and anodes 150 in accordance with an embodiment of the present disclosure. The stack (illustrated in an exploded view in FIG. 2A) includes a plurality of anodes 150 stacked together. Each plurality of anodes 150 is separated by a single cathode 120 which is disposed between two separators 140. A plan view of the stack is illustrated in FIG. 2B. The recesses 136, 146, and 156 of the cathodes 120, separators 140, and anodes 150 are, respectively, aligned with each other in the stack. As discussed herein, the recesses 146 and 156 are responsible for the alignment of the separators 140 and the anodes 150 within the stack. The tails 126 of the cathodes 120 are in alignment with one another, as are the tails 128. As discussed herein, the recesses 134 in the tails 126, 128 are responsible for alignment of the cathodes 120 within the stack.

Figure 3:
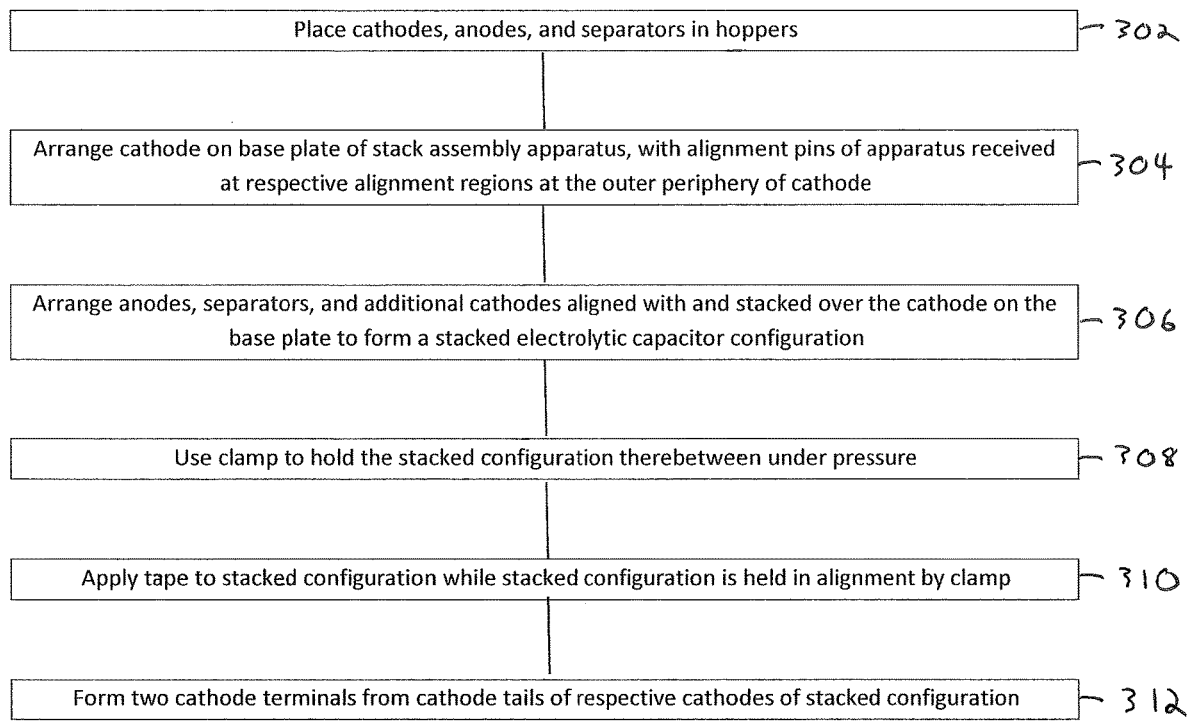
FIG. 3 is a flowchart of a process for manufacturing a stacked electrolytic capacitor configuration according to an embodiment of the present disclosure.

The flowchart of FIG. 3 illustrates a process 300 according to an embodiment of the present disclosure for manufacturing a stacked electrolytic capacitor configuration including one or more cathodes as described herein. The capacitor stack is described below as being assembled using pluralities of cathodes 120, separators 140, and anodes 150.

Process 300 may be performed, for example, using a stack assembly apparatus 500 as illustrated in FIGS. 4, 5A and 5B. Referring to FIGS. 4, 5A and 5B, the stack assembly apparatus 500 may include an arm 502 interconnecting a support base 504 and a stacking fixture or base plate 506. Holes 508 may extend through the thickness of the base plate 506 between a top surface 514 and a bottom surface 510, and may be configured to receive alignment elements or pins 512 that extend from an alignment block 513, which is below the bottom surface 510 of the base plate, to above the top surface 514 of the base plate. The alignment block 513 may further include cathode tail alignment pins 522, which extend above the top surface 514 of the base plate. Each of the alignment elements or pins 512 may be configured such that an external surface portion thereof facing an interior region of the base plate 506 has a shape corresponding to the shape of alignment recesses 146 and 156 at the peripheral edges of the separators 140 and anodes 150, respectively, and the pins 512 may be positioned to reside within these alignment recesses. In addition, the pins 522 may be configured and positioned to reside within the recesses 134 of the tails 126, 128 of the cathode 120 when the cathode is included in a stack formed on the base plate 506.

Referring to FIG. 3, in block 302, a plurality of cathodes 120, separators 140, and anodes 150 may be placed in separate hoppers for assembly into a stack using the apparatus 500 or, alternatively, for use in a manual process of stack assembly.

In block 304, a cathode 120 from the hopper may be disposed on top surface 514 of the base plate 506 of the stack assembly apparatus 500, such as by operation of a robotic assembly device. In particular, the cathode 120 may be arranged on the base plate 506 such that each recess 136 is aligned with a corresponding alignment pin 512. The recesses 136 being inward of the recesses 146, 156 of the separator 140 and anode 150 do not contact the alignment pins 512, which are used for self-alignment of the separators 140 and the anodes 150, such as when each of such components is placed one over the other to form a stack. The recesses 134 in the tails 126, 128 may receive the alignment pins 522 therein, which provides for self-alignment of the cathodes 120 in the stack.

In block 306, an electrode stack may be created by adding one or more separators 140, anodes 150, and cathodes 120 one over the other, such as on top of the cathode 120 initially disposed directly on the top surface 514 of the base plate 506. The stack may include any number of anodes, in any desired arrangement with the respect to the cathodes. In one embodiment, the anode may be an etched foil having an outer periphery with the same configuration as the peripheral edge of the separator 140. The alignment regions of the separator 140, and similar and corresponding alignment regions that may be provided at the peripheral edge of the anode 150, may provide for self-alignment of these components in the stack. Further, based on the creation of a stack including cathodes, separators together with multiple anodes aligned with one another by the alignment regions, as well as cathodes having a pair of tails, 126, 128 peripheral edge tolerances for the stack may be about +/−0.001 to 0.002 inches. A two tail cathode may provide superior tolerance and yield (for example as compared to a single tail alignment system) owing to less degrees of freedom when the cathode is stacked such that a misalignment outside of the tolerance is less likely to occur. With such tolerances in the manufacture of a stack according to the present disclosure, a high packaging efficiency may be obtained for anodes included in the stack, because an anode having an increased functional surface area may be placed within the same volume of a stack.

Referring again to FIG. 3, in block 308, after a desired stack of anodes, separators, and cathodes in alignment with one another at their respective peripheral edges is formed in block 306, one or more clamps 516 may be used to hold the stack together and avoid the components of the stack from becoming misaligned before the stack is placed, for example, in the case of a battery. The clamp 516 may include a top clamping surface 517A and a bottom clamping surface 517B. The surface 517B may be positioned at the bottom surface 510 of the base plate 506, and a tamp 515 may then be positioned on top of the stack with the surface 517A positioned in a recess 515A of the tamp, such that the stack is held fixed in position between the tamp 515 and the top surface 514 of the base plate, and the components of the stack are not permitted to move and become misaligned with other components in the stack. The use of multiple clamps 516 advantageously allows uniform pressure to be applied to the stack at multiple points to insure equal compression within the stack, which also improves packaging efficiency for the stack.

In block 310, tape or an external boot may be applied to maintain the aligned arrangement of the elements of the stack while the stack is held fixed by the clamps 516 under pressure. Then, the clamps may be suitably removed and a stacked electrolytic capacitor configuration, with the alignment of the cathodes and anodes maintained by the tape, may undergo further manufacturing processing.

In one embodiment, referring to FIGS. 6A and 6B, an electrolytic capacitor configuration or stack 600 obtained in block 310 may include a cathode 120 at each of the top and bottom of the stack 600, a separator 140 adjacent an interior surface of each of the top and bottom cathodes 120 in the stack, and several sets of multiple anodes 150 along with cathodes 120 and separators 140. Adjacent sets of anodes may be separated by a separator 140, a cathode 120, and another separator 140. The anodes and separators in the stack may have alignment regions at the outermost peripheral edge thereof to provide for self-alignment, and the cathodes may have alignment regions (i.e., the tails 126, 128) to provide for self-alignment. Using these alignment regions, all components of the stack can be aligned with one another.

Referring to FIGS. 7A and 7B, in further steps of the manufacture of a stacked electrolytic capacitor configuration according to the present disclosure, a stack, such as the stack 600 of FIGS. 7A and 7B, may, by automatic or manual means, be configured to fit into a battery device by joining tails 126, 128 of the cathodes 120 to one another. Referring to FIG. 3, in block 312, single cathode terminals 700 may be formed from the cathode tails 126, 128 by compressing the cathode tails on one side of the stack 600 together, bending the compressed cathode tails towards an adjacent peripheral edge of the stack and into contact with the cathode 120 at the other end of the stack, and then welding the cathode tails of the stack together. When the cathode tails are being compressed together on one side of the stack, and when the cathode tails are in an assembled position, welded together and extending along the peripheral edge of the stack to form the terminals 700, the portions of the separators 140 at the edge portions 148 may provide barriers that avoid contact, and maintain a minimum line of sight, between edges of the anodes 150 and the exposed surfaces of the cathode tails, so as to avoid arc discharge or shorting between the former and latter. The edge portions 148 of the separators 140, as discussed above, may be configured to have a size and shape such that the edge portions 148 in a stack create a line of sight and contact barrier in view of the expected bending of the cathode tails during the manufacture of a stack. After the cathode tails are welded together, the stack may be placed into a capacitor housing. The two tail cathode may further provide an additional benefit of a lower resistance due to the added connection to the housing provided by a second tail.

It is to be understood that the embodiments of capacitors disclosed herein are merely illustrative of the principles and applications of the present disclosure.

Advantageously, the present disclosure may provide for the manufacture of a stacked electrolytic capacitor configuration whose components are self-aligned, without the use of complex internal mechanical features of alignment within an interior region of the components of the stack, such as the anodes or cathodes, which may compromise performance, because the functional surface area of the components is replaced by alignment features, such as apertures in the functional areas.

To summarize, the present disclosure describes a cathode comprising a conductive sheet having a central portion defined by a peripheral edge, a first tail extending out from the peripheral edge in a first direction, and a second tail extending out from the peripheral edge in a second direction opposite the first direction, wherein each of the first tail and the second tail has a first recess at a free end thereof; and/or the conductive sheet includes at least two second recesses extending inward from the peripheral edge of the central portion, one of the second recesses being located adjacent to a connected end of the first tail, and another of the second recesses being located adjacent to a connected end of the second tail; and/or the conductive sheet includes a first pair of second recesses extending inward from the peripheral edge of the central portion adjacent to and on opposite sides of a connectedend of the first tail; and a second pair of second recesses extending inward from the peripheral edge of the central portion adjacent to and on opposite sides of a connected end of the second tail; and/or each of the first tail and the second tail has a pair of first recesses at the free end thereof.

Also described herein is a device comprising a conductive anode; a dielectric material disposed on a surface of the conductive anode; a conductive cathode; a separator disposed between the anode and the cathode; and an electrolyte disposed between the anode and the cathode, wherein the conductive cathode includes a first conductive sheet having a central portion defined by a peripheral edge; a first tail extending out from the peripheral edge in a first direction; and a second tail extending out from the peripheral edge in a second direction opposite the first direction, wherein each of the first tail and the second tail has a first recess at a free end thereof; and/or the cathode further includes a first pair of second recesses extending inward from the peripheral edge of the central portion adjacent to and on opposite sides of a connected end of the first tail; and a second pair of second recesses extending inward from the peripheral edge of the central portion adjacent to and on opposite sides of a connected end of the second tail; and/or each of the first tail and the second tail has a pair of first recesses at the free end thereof; and/or the cathode further includes at least two second recesses extending inward from the peripheral edge of the central portion, one of the second recesses being located adjacent to a connected end of the first tail, and another of the second recesses being located adjacent to a connected end of the second tail; and/or the separator comprises a non-conductive sheet defined by a peripheral edge; and at least two third recesses extending inward from the peripheral edge of the non-conductive sheet; and/or the second recesses of the cathode are aligned with the third recesses of the non-conductive sheet; and/or the separator comprises a non-conductive sheet defined by a peripheral edge; a first pair of third recesses extending inward from the peripheral edge on one side of the non-conductive sheet and defining a first edge portion between the first pair of third recesses; and a second pair of third recesses extending inward from the peripheral edge on a side of the non-conductive sheet opposite the one side and defining a second edge portion between the second pair of third recesses; and/or the first edge portion is aligned with the first tail and the second edge portion is aligned with the second tail; and/or the anode comprises a second conductive sheet defined by a peripheral edge; and at least two fourth recesses extending inward from the peripheral edge of the second conductive sheet; and/or the second recesses of the cathode are aligned with the fourth recesses of the second conductive sheet; and/or the anode comprises a second conductive sheet defined by a peripheral edge; a first pair of fourth recesses extending inward from the peripheral edge on one side of the second conductive sheet and defining a first edge portion between the first pair of fourth recesses; and a second pair of fourth recesses extending inward from the peripheral edge on a side of the second non-conductive sheet opposite the one side defining a second edge portion between the second pair of fourth recesses; and/or the first edge portion is aligned with the first tail and the second edge portion is aligned with the second tail; and/or the device is an electrolytic capacitor; and/or the separator is permeable to the electrolyte.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A cathode, comprising:
   a conductive sheet having a central portion defined by a peripheral edge,
   a first tail extending out from the peripheral edge in a first direction, and
   a second tail extending out from the peripheral edge in a second direction opposite the first direction,
   wherein each of the first tail and the second tail has a first recess at a free end thereof.

2. The cathode of claim 1, wherein the conductive sheet includes:
   at least two second recesses extending inward from the peripheral edge of the central portion, one of the second recesses being located adjacent to a connected end of the first tail, and another of the second recesses being located adjacent to a connected end of the second tail.

3. The cathode of claim 1, wherein the conductive sheet includes:
   a first pair of second recesses extending inward from the peripheral edge of the central portion adjacent to and on opposite sides of a connected end of the first tail; and
   a second pair of second recesses extending inward from the peripheral edge of the central portion adjacent to and on opposite sides of a connected end of the second tail.

4. The cathode of claim 3, wherein each of the first tail and the second tail has a pair of first recesses at the free end thereof.

5. A device, comprising:
   a conductive anode;
   a dielectric material disposed on a surface of the conductive anode;
   a conductive cathode;
   a separator disposed between the anode and the cathode; and
   an electrolyte disposed between the anode and the cathode,
   wherein the conductive cathode includes:
      a first conductive sheet having a central portion defined by a peripheral edge;
      a first tail extending out from the peripheral edge in a first direction; and
      a second tail extending out from the peripheral edge in a second direction opposite the first direction,
      wherein each of the first tail and the second tail has a first recess at a free end thereof.

6. The device of claim 5, wherein the cathode further includes:
   a first pair of second recesses extending inward from the peripheral edge of the central portion adjacent to and on opposite sides of a connected end of the first tail; and
   a second pair of second recesses extending inward from the peripheral edge of the central portion adjacent to and on opposite sides of a connected end of the second tail.

7. The device of claim 6, wherein each of the first tail and the second tail has a pair of first recesses at the free end thereof.

8. The device of claim 5, wherein the cathode further includes:
   at least two second recesses extending inward from the peripheral edge of the central portion, one of the second recesses being located adjacent to a connected end of the first tail, and another of the second recesses being located adjacent to a connected end of the second tail.

9. The device of claim 8, wherein the separator comprises:
a non-conductive sheet defined by a peripheral edge; and
at least two third recesses extending inward from the peripheral edge of the non-conductive sheet.

10. The device of claim 9, wherein the second recesses of the cathode are aligned with the third recesses of the non-conductive sheet.

11. The device of claim 8, wherein the separator comprises:
a non-conductive sheet defined by a peripheral edge;
a first pair of third recesses extending inward from the peripheral edge on one side of the non-conductive sheet and defining a first edge portion between the first pair of third recesses; and
a second pair of third recesses extending inward from the peripheral edge on a side of the non-conductive sheet opposite the one side and defining a second edge portion between the second pair of third recesses.

12. The device of claim 11, wherein the first edge portion is aligned with the first tail and the second edge portion is aligned with the second tail.

13. The device of claim 8, wherein the anode comprises:
a second conductive sheet defined by a peripheral edge; and
at least two fourth recesses extending inward from the peripheral edge of the second conductive sheet.

14. The device of claim 13, wherein the second recesses of the cathode are aligned with the fourth recesses of the second conductive sheet.

15. The device of claim 8, wherein the anode comprises:
a second conductive sheet defined by a peripheral edge;
a first pair of fourth recesses extending inward from the peripheral edge on one side of the second conductive sheet and defining a first edge portion between the first pair of fourth recesses; and
a second pair of fourth recesses extending inward from the peripheral edge on a side of the second non-conductive sheet opposite the one side defining a second edge portion between the second pair of fourth recesses.

16. The device of claim 15, wherein the first edge portion is aligned with the first tail and the second edge portion is aligned with the second tail.

17. The device of claim 5, wherein the device is an electrolytic capacitor.

18. The device of claim 5, wherein the separator is permeable to the electrolyte.

* * * * *